United States Patent [19]
Albertini et al.

[11] Patent Number: 6,113,903
[45] Date of Patent: Sep. 5, 2000

[54] PEPTIDES AND METHODS AGAINST DIABETES

[75] Inventors: Richard J. Albertini, Underhill Center; Michael T. Falta, Hinesburg, both of Vt.

[73] Assignee: The Immune Response Corporation, Carlsbad, Calif.

[21] Appl. No.: 08/195,963

[22] Filed: Feb. 14, 1994

Related U.S. Application Data

[63] Continuation-in-part of application No. 08/182,416, Jan. 14, 1994, Pat. No. 5,482,837, application No. 08/813,867, Dec. 24, 1991, abandoned, and application No. 07/644,611, Jan. 22, 1991, abandoned, which is a continuation-in-part of application No. 07/530,229, May 30, 1990, abandoned, which is a continuation-in-part of application No. 07/382,085, Jul. 18, 1989, abandoned, and application No. 07/382,086, Jul. 18, 1989, abandoned, which is a continuation-in-part of application No. 07/326,314, Mar. 21, 1989, abandoned, said application No. 07/382,085, is a continuation-in-part of application No. 07/326,314.

[51] Int. Cl.[7] .................................................. A61K 38/00
[52] U.S. Cl. ........................ 424/185.1; 530/300; 530/350; 530/395
[58] Field of Search ............................. 424/184.1, 185.1, 424/278.1; 514/2, 12–16, 44; 530/300, 324–9, 868; 435/320.1

[56] References Cited

U.S. PATENT DOCUMENTS

| | | | |
|---|---|---|---|
| 4,066,510 | 1/1978 | Thilly | 435/6 |
| 4,544,632 | 10/1985 | Yamamura et al. | 435/948 |
| 4,647,535 | 3/1987 | Ritts, Jr. | 435/948 |
| 4,886,743 | 12/1989 | Hood et al. | 435/5 |
| 5,112,735 | 5/1992 | Albertini | 435/6 |
| 5,436,319 | 7/1995 | Kung | 530/350 |
| 5,552,300 | 9/1996 | Makrides et al. | 435/69.1 |
| 5,612,035 | 3/1997 | Howell et al. | 424/185.1 |
| 5,614,192 | 3/1997 | Vanderbark | 424/185.1 |
| 5,643,868 | 7/1997 | Weiner | 514/3 |

FOREIGN PATENT DOCUMENTS

| | | |
|---|---|---|
| 0 340 109 | 2/1989 | European Pat. Off. . |
| 0340109 A2 | 4/1989 | European Pat. Off. . |
| WO 89/06968 | 10/1989 | WIPO . |
| WO-91/01133 | 2/1991 | WIPO . |
| WO-87/03600 | 6/1997 | WIPO . |

OTHER PUBLICATIONS

Ames and Gold, "Chemical Carcinogenesis: Too Many Rodent Carcinogens," *Proc. Natl. Acad. Sci.* 87:7772–7776 (1990).

Allegretta et al., "T cells responsive to myelin basis protein in patients with multiplesclerosis," *Science* 247:718–721 (1990).

Ben–Nun et al., "Vaccination against autoimmune encephalomyelitis with T–lymphocyte line cells reactive against myelin basic protein," *Nature* 292:60–61 (1981).

Bottazzo et al., "In situ characterization of autoimmune phenomena and expression of HLA molecules in the pancreas in diabetic insulitis," *N. Engl. J. Med.* 313(6):353–360 (1985).

Clark et al., *Ann. Neurol.* 31:587–592 (1992).
Concannon et al., *PNAS* 83:6598 (1986).
Edouard et al., *Eur. J. Immunol.* 23:727–733 (1993).
Ertl et al., *Viral Immunol.* 9(1):1–9 (1996).
Esch et al., "Observations, legends, and conjectures concerning restricted T–cell receptor usage and autoimmune disease" *Crit. Rev. Immunol.* 11:349 (1992).
Friedman et al., *J. Exp. Med.* 174:891–900 (1991).
Giegrich et al., *Eur. J. Immunol.* 22:753–758 (1992).
Gmelig–Meyling et al., "Assessment of In Vivo Frequency of Mutated Cells in patients with systemic lupus erythematosus," *J. Exp. Med.* 175:297–300 (1992).
Graur et al., *Science* 249:91–94 (1993).
Gregorian et al., *FASEB J.* 6:A1685 (1992).
Grunewald et al., *Scand. J. Immunol.* 34:161–168 (1992).
Grunewald et al., *Eur. J. Immunol.* 22:129–135 (1992).
Hafler, *Immunol. Today* 17:152 (1996).
Hanninen et al., *J. Clin. Invest.* 90:1961 (1992).
Howell et al., *Proc. Natl. Acad. Sci. USA* 88:10921–10925 (1991).
Infante et al., *J. Immunol.* 148:3385–3390 (1992).
Kappler et al., "A T–cell receptor V–beta segment that imparts reactivity to a class II major histocompatibility complex product." *Cell* 49:263–271 (1987).
Karin et al., *J. Exp. Med.* 180:2227 (1994).
Kawano et al., *Cancer Eye Res.* 10:789–795 (1991).
Lahesma et al., *J. Immunol.* 150:4125–4135 (1993).
Lee et al., *Ann Neurol.* 29:33–40 (1991).
Malhorta et al., "Variability in T cell receptor vβ gene usage in human peripheral blood lymphocytes." *J. Immunology* 149:1802–1808 (1992).
Martin et al., *J. Immunol.* 148:1359 (1992).
McKeever et al., *J. Exp. Med.* 184:1755 (1996).
Newsom–Davis, *J. Auto Immunity* 2:101 (1989).
Nicklas et al., "Use of T–cell receptor gene probes to quantify the in vivo hprt mutations in human T–lymphocytes." *Mutation Res.* 173:67–72.

(List continued on next page.)

*Primary Examiner*—Thomas M. Cunningham
*Attorney, Agent, or Firm*—Campbell & Flores LLP

[57] ABSTRACT

This invention relates to methods of preventing or reducing the severity of diabetes. In one embodiment, the method involves administering to the individual a peptide having substantially the sequence of a on-conserved region sequence of a T cell receptor present on the surface of T cells mediating diabetes or a fragment thereof, wherein the peptide or fragment is capable of causing an effect on the immune system to regulate the T cells. In particular, the T cell receptor has the Vβ regional Vβ6 or Vβ14. In another embodiment, the method involves gene therapy. The invention also relates to methods of diagnosing diabetes by determining the presence of diabetes predominant T cell receptors.

18 Claims, 7 Drawing Sheets

OTHER PUBLICATIONS

Nicklas et al., "Molecular Analyses of In Vivo Hypoxanthine–Guanine Phosphoribosyltrasferase Mutations in Human T–Lymphocytes: II. Demonstration of a Clonal Amplification of hprt Mutant T–Lymphocytes In Vivo." *Env. And Mol. Mut.* 12:271–284 (1988).

Nishimoto et al., "Prevention of autoimmune insulitis by expression of I–E molecules in NOD mice," *Nature* 328:432–434 (1987).

Paliard et al., *Science* 253:325–329 (1991).

Patten et al., "Structure, expression and divergence of T–cell receptor β–chain variable regions." *Nature* 312:40–46 (1984).

Posnett et al., *J. Clin. Invest.* 85:1770–1776 (1990).

Prigione et al., *Fund. Clin. Immunol.* 2:161 (1994).

Vandenbark et al., "Immunization with a synthetic T–cell receptor V–region peptide protects against experimental autoimmune encephalomyelitis." *Nature* 341:541–544 (1989).

Shoenfeld et al., "Immunological and genetic factors in autoimmune diseases." *N. Engl. J. Med.* 311(16) :1019–1029 (1984).

Sellins et al., *J. Immunol.* 149:2323–2327 (1992).

Smith et al., *Blood* 81:1521–1526 (1993).

Tanuma et al., *J. Exp. Med.* 168:85–90 (1996).

Urban et al., "Restricted use of T cell receptor V genes in murine autoimmune encephalomyelitis raises possibilities for antibody therapy." *Cell* 54:577–592 (1988).

Welch et al., *J. Immunol.* 125:186 (1993).

Yang et al., "Molecular Evidence For New Mutation at the hprt Locus in Lesch–Nyhan Patients," *Nature* 310:412–414 (1984).

Abe et al., *Proc. Natl. Acad. Sci. U.S.A.* 89:4066–4070 (1992).

Albertini et al., "T–Cell cloning to detect the mutant 6–thioquanine–resistant lymphocytes present in human peripheral blood," *PNAS, USA* 79:6617–6621 (1982).

Albertini et al.., "Alterations of the hprt gene in human in–vivo–derived 6–thioguanine–resistant T lymphocytes," *Nature* 316:369–371 (1985).

Ames and Gold, "Too Many Rodent Carcinogens: Mitogenesis Increases Mutagenesis," *Science* 249:970–971 (1990).

Albertini et al., "T–Cell cloning to detect the mutant 6–thioguanine–resistant lymphocytes present in human peripheral blood." *PNAS, USA* 79:6617–6621 (1982).

Yanagi et al., "A human T cell–specific cDNA clone encodes a protein having extensive homology to immunoglobulin chains." *Nature* 308:145–149 (1984).

Albertini et al., "Alterations of the hprt gene in human in–vivo–derived 6–thioguanine–resistant T lymphocytes." *Nature* 316:369–371 (1985).

Nicklas, et al., "Use of T–cell receptor gene probes to quantify the in vivo Hprt mutations in human T–lymphocytes." *Mutation Res.* 173:67–72.

Gmelig–Meyling et al., "Assessment of In Vivo Frequency of Mutated T Cells in Patients with Systemic Lupus Erythematosus." *J. Exp. Med.* 175:297–300 (1992).

Ames and Gold, "Too Many Rodent Carcinogens: Mitogenesis Increases Mutagenesis." *Science* 249:970–971 (1990).

Ames and Gold, "Chemical Carcinogenesis: Too Many Rodent Carcinogens." *Proc. Natl. Acad. Sci.* 87:7772–7776 (1990).

Hafler, D. A. et al., Immunology Today 17(4):152–159 (Apr., 1996), "TCR usage in human and experimental demyelinating disease", Apr. 1996.

Ben–Nun, A. et al., Nature 292:60–61 (1981), "Vaccination against autoimmune encephalomyelitits with T–lymphocyte line cells reactive against myelin basic protein".

.Bottazzo, G. F., et al., N. Engl. J. med. 313(6):353–360 (1985), "In situ characterization of autoimmune phenomena and expression of HLA molecules in the pancreas in diabetic insulitis".

Esch, T., et al., Critical Reviews in Immunology 11(5):249–264 (1992), "Observations, legends, and conjectures concerning restricted T–cell receptor usage and autoimmune disease".

Kappler, J. W., et al., Cell 49:263–271 (1987), "A T–cell receptor V–beta segment that imparts reactivity to a class II major histocompatibility complex product".

Nishimoto, H., et al., Nature 328:432–434 (Jul. 30, 1987), "Prevention of autoimmune insulitis by expression of I–E molecules in NOD mice".

Shoenfeld, Y., et al., N. Engl. J. Med, vol. 311 (16): 1019–1029 (Oct., 1984), "Immunological and genetic factors in autoimmune diseases".

Urban, J. L., et al., Cell 54: 577–592 (1988), "Restricted use of T cell receptor V genes in murine autoimmune encephalomyelitis raises possibilities for antibody therapy".

Vandenbark, A. A., et al., Nature 341:541–544 (Oct. 12, 1989), "Immunization with a synthetic T–cell receptor V–region peptide protects against experimental autoimmune encephalomyelitis".

TCR Vβ's OF INTEREST IN IDDM

Vβ 6.1

GAGVSQTPSNKVTEKGKYVELRCDPISGHTALY
WYRQSLGQGPEFL<u>IYFQGTGAADDSGL</u>PNDRFF
AVRPEGSVSTLKIQRTERGDSAVYLCASS

Vβ6.6/6.7

GAGVSQSPSNKVTEKGKDVELRCDPISGHTAL
YWYRQSLGQFLEFL<u>IYFQGNSAPDKSGL</u>PSDRGSA
ERTGGSVSTLTIQRTQQEDSAVYLCASS

Vβ14

EAQVTQNPRYLITVTGKKLTVTCSQNMNHEYMSW
YRQDPGLGLRQI<u>YYSMNVEVTDKGD</u>VPEGYKVSRK
EKRNFPLILESPSPNQTSLYFCASR

The underlined sequences contain the CDR2 region.

TCR Vβ'S interest in IDDM

Vβ 6.1

GGTGCTGGAGTCTCCCAGACCCCCAGTAACAAGGTCACAGAGAAGGGAAAATATGTA
GAGCTCAGGTGTGATCCAATTTCAGGTCATACTGCCCTTTACTGGTACCGACAAAG
CCTGGGGCAGGGCCCAGAGTTTCTAATTTACTTCCAAGGCACGGGTGCGGCAGATG
ACTCAGGGCTGCCCAACGATCGGTTCTTTGCAGTCAGGCCTGAGGGATCCGTCTCT
ACTCTGAAGATCCAGCGCACAGAGCGGGGGGACTCAGCCGTGTATCTCTGTGCCAG
CAGC

CDR2 Amino Acid Sequence: IYFQGTGAADDSGL

Vβ 6.6/6.7

GGAGCTGGAGTTTCCCAGTCCCCCAGTAACAAGGTCACAGAGAAGGGAAAGGATG
TAGAGCTCAGGTGTGATCCAATTTCAGGTCATACTGCCCTTTACTGGTACCGACAG
AGCCTGGGGCAGGGCCTGGAGTTTTTAATTTACTTCCAAGGCAACAGTGCACCAGA
CAAATCAGGGCTGCCCAGTGATCGCTTCTCTGCAGAGAGGACTGGGGGATCCGTCT
CCACTCTGACGATCCAGCGCACACAGCAGGAGGACTCGGCCGTGTATCTCTGTGCC
AGCAGC

CDR2 Amino Acid Sequence: IYFQGNSAPDKSGL

Vβ 14.1

GAAGCCCAAGTGACCCAGAACCCAAGATACCTCATCACAGTGACTGGAAAGAAGT
TAACAGTGACTTGTTCTCAGAATATGAACCATGAGTATATGTCCTGGTATCGACAA
GACCCAGGGCTGGGCTTAAGGCAGATCTACTATTCAATGAATGTTGAGGTGACTGA
TAAGGGAGATGTTCCTGAAGGGTACAAAGTCTCTCGAAAAGAGAAGAGGAATTTCC
CCCTGATCCTGGAGTCGCCCAGCCCCAACCAGACCTCTCTGTACTTCTGTGCCAGC
AGG

CDR2 Amino Acid Sequence: YYSMNVEVTDKGDV

CDR2 region defined as amino acid residues 47--60 by
Chothia et, al, EMBO Vol 7(12), pp3745-3755, 1988

FIG. 7

PEPTIDES AND METHODS AGAINST DIABETES

This invention is a continuation-in-part of U.S. Ser. No. 07/644,611, filed Jan. 22, 1991 (now abandoned), which is a continuation-in-part of U.S. Ser. No. 07/530,229, filed May 30, 1990 (now abandoned), which is a continuation-in-part of U.S. Ser. Nos. 07/382,085 (now abandoned) and 07/382,086 (now abandoned), both filed on Jul. 18, 1989, which are continuations-in-part of U.S. Ser. No. 07/326,314, filed Mar. 21, 1989 (now abandoned), and is also a continuation-in-part of U.S. Ser. No. 08/182,416, filed Jan. 14, 1994 now U.S. Pat. No. 5,482,837 and a c.i.p. of U.S. application Ser. No. 08/813,867, filed Dec. 24, 1991 (now abandoned). All of these prior applications are incorporated herein.

This invention was made with government support under ER 60502 awarded by the Department of Energy and CA 30688 awarded by the National Cancer Institute. The government has certain rights in the invention.

BACKGROUND OF THE INVENTION

This invention relates to the immune system and, more specifically, to methods of modifying pathological immune responses in diabetes.

Higher organisms are characterized by an immune system which protects them against invasion by potentially deleterious substances or microorganisms. When a substance, termed an antigen, enters the body and is recognized as foreign the immune system mounts both an antibody-mediated response and a cell-mediated response. Cells of the immune system termed B lymphocytes, or B cells, produce antibodies that specifically recognize and bind to the foreign substance. Other lymphocytes termed T lymphocytes, or T cells, both effect and regulate the cell-mediated response, resulting eventually in the elimination of the antigen.

A variety of T cells are involved in the cell-mediated response. Some induce particular B cell clones to proliferate and produce antibodies specific for the antigen. Others recognize and destroy cells presenting foreign antigens on their surfaces. Certain T cells regulate the response by either stimulating or suppressing other cells.

While the normal immune system is closely regulated, aberrations of the response are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly effect such autoimmune pathologies. T cells have on their surface proteins known as T cell receptors (TCR) which mediate the recognition of and activity by antigen.

Diabetes can be an autoimmune disease in which the immune system attacks critical cells of the pancreas interfering normal regulation. Insulin-dependent diabetes mellitus (IDDM), also known as type I or juvenile onset diabetes, is one such autoimmune disease which can have devastating results. While the primary effect of the disease can be controlled by administration of the insulin, secondary affects of the disease and such effects of the treatment reduce both the length and quality of life. It is estimated that there are more than a million IDDM patients in the United States alone.

A need exists for improved and effective means of curing or ameliorating diabetes. Such a treatment should ideally control the inappropriate T cell response, rather than merely reducing the symptoms. The present invention satisfies this need and provides related advantages as well.

SUMMARY OF THE INVENTION

This invention provides composition and methods of preventing or reducing the severity of diabetes in an individual by administering a T cell receptor, or fragment thereof having substantially the sequence of a T cell receptor present on the surface of T cells mediating diabetes which is capable of causing an effect on the immune system to regulate the T cells. The particular TCRs are preferably administered as peptides corresponding to the amino acid sequence of non-conserved regional of the TCR, although particular whole TCRs or T Cells bearing specific TCRs can also be administered.

According to another embodiment, the method involves preventing or reducing the severity of diabetes by inhibiting the binding of a T cell receptor to its TCR binding partner in order to prevent the proliferation of T cells associated with diabetes.

This invention also provides methods of preventing or reducing the severity of diabetes in an individual by contacting T cells specifically associated with diabetes with an effective amount of a cytotoxic or cytostatic agent specifically reactive with such T cells to inhibit their activity.

This invention further provides methods of diagnosing or predicting susceptibility to diabetes in an individual by detecting T cells having a T cell receptor associated with diabetes in a sample from the individual, the presence of abnormal expression of T cells containing the T cell receptor indicating the pathology or susceptibility to diabetes.

This invention also provides vectors having an expression control sequence operatively linked to a nucleic acid encoding a T cell receptor or a peptide having substantially the sequence of a non-conserved region sequence of a T cell receptor present on the surface of T cells mediating diabetes. These vectors can be used to achieve expression of the peptide in an individual having or at risk of having diabetes.

DETAILED DESCRIPTION OF THE INVENTION

This invention provides compositions and methods for preventing or reducing the severity of diabetes. The invention results from the discovery that diabetes is characterized by the predominant usage of certain T cell receptors. In particular, Vβ6.1, Vβ6.6/6.7 and Vβ14 predominate. Treatment according to the method of the invention provides a specific and sustained amelioration which avoids problems associated with other potential avenues of therapy.

As used herein, "substantially the amino acid sequence," or "substantially the sequence" when referring to an amino acid sequence means the described sequence or other sequences having additions, deletions or substitutions that do not substantially effect the ability of the sequence to cause an effect on the immune system which regulates T cells having the desired T cell receptor. Such sequences commonly contain additional amino acid sequences adjacent to the described sequence.

A portion or segment of the described sequence can also be used in the invention so long as it is sufficiently characteristic of the desired T cell receptor or fragment thereof to cause an effect on the immune system which regulates T cells having the desired T cell receptors, but not against T cells not having desired T cell receptors. Such variations in the sequence can easily be made, for example by synthesizing an alternative sequence. The alternate sequence can then be tested, for example by administration to a vertebrate, to determine its effectiveness.

As used herein, the term "fragment" means a subset of the non-conserved amino acid sequence of a TCR that can cause an effect on the immune system which regulates T cells. As used herein, the term "non-conserved region" refers to variable and VDJ regions. The term is intended to include such fragments in conjunction with or combined with additional sequences or moieties, as for example where the peptide is coupled to other amino acid sequences or to a carrier. The terms "fragment" and "peptide" can, therefore, be used interchangeably since a peptide will be the most common fragment of the T cell receptor. Each fragment of the invention can have an altered sequence, as described above for the term "substantially the sequence."

Reference herein to a "fragment," "portion" or "segment" of a T cell receptor does not mean that the composition must be derived from intact T cell receptors. Such "fragments," "portions" or "segments" can be produced by various means well-known to those skilled in the art, such as, for example, manual or automatic peptide synthesis, various methods of cloning or enzymatic treatment of a whole TCR.

As used herein, the phrase to "cause an effect on the immune system which regulates T cells" means to cause the immune system to modify the activity in response to their ligands of T cells bearing particular T cell receptors. Such an effect can include either wholly or partially a T cell response. For example, the down regulation of an autoreactive T cell may be a result of the recognition by a regulatory T cell of the T cell receptor peptide in the groove of an MHC molecule on the surface of an autoreactive T cell. Alternatively, the regulatory effect can be caused by the interference by a T cell receptor peptide of the interaction of a T cell receptor on an autoreactive T cell and its MHC/peptide ligand. Such modification of activity can be evidenced by amelioration of the severity of inflammation in the target tissue. The amount of such a peptide necessary to cause such an effect will vary between species and individuals depending on many factors which one skilled in the art can determine.

As used herein, "binding partner" means a compound which is reactive with a TCR. Generally, this compound will be a Major Histocompatibility Antigen (MHC) but can be any compound capable of directly or indirectly stimulating T cell activation or proliferation when bound to the TCR. Such compounds can also be, for example, a superantigen that binds to a superantigen binding site on the TCR.

As used herein, "superantigens" means antigens or fragments thereof that bind preferentially to T cells at specific sites on the $\beta$ chain of a TCR and stimulate T cells at very high frequency rate. Such superantigens can be endogenous or exogenous. "Frequency" refers to the proportion of T cells responding to antigens and ranges from about $\frac{1}{5}$ to $\frac{1}{100}$ in response to superantigens. Thus, superantigens are distinguishable from conventional antigens, which have a much lower T cell response frequency rate ranging from about $\frac{1}{10^4}$ to $\frac{1}{10^6}$. Superantigens activate T cells by binding to specific V$\beta$s. The superantigen binding sites of various TCRs have been distinguished from the conventional hypervariable regions (CDRs) of TCRs. These CDRs represent the regions of TCRs thought to be responsible for binding conventional antigens that are complexed to MHC.

As used herein, "ligand" means any molecule that reacts with another molecule to form a complex.

As used herein, "selectively binds" means that a molecule binds to one type of molecule or related group of molecules, but not substantially to other types of molecules. In relation to V$\beta$s, "selective binding" indicates binding to TCRs or fragments thereof containing specific V$\beta$ without substantial cross-reactivity with other TCRs that lack the specific V$\beta$.

As used herein, "individual" means any vertebrate, including human, capable of having diabetes.

As used herein, "reduce the severity of diabetes" means improving the condition of the patients or decreasing the percentage of T cells bearing a preferential T cell receptor.

The immune system is the primary biological defense of the host (self) against potentially pernicious agents (non-self). These pernicious agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

T cells owe their antigen specificity to the T cell receptor (TCR) which is expressed on the cell surface. The TCR is a heterodimeric glycoprotein, composed of two polypeptide chains, each with a molecular weight of approximately 45 kD. Two forms of the TCR have been identified. One is composed of an alpha chain and a beta chain, while the second consists of a gamma chain and a delta chain. Each of these four TCR polypeptide chains is encoded by a distinct genetic locus containing multiple discontinuous gene segments. These include variable (V) region gene segments, joining (J) region gene segments and constant (C) region gene segments. Beta and delta chains contain an additional element termed the diversity (D) gene segment. Since D segments and elements are found in only some of the TCR genetic loci, and polypeptides, further references herein to D segments and elements will be in parentheses to indicate the inclusion of these regions only in the appropriate TCR chains. Thus, V(D)J refers either to VDJ sequences of chains which have a D region or refers to VJ sequences of chains lacking D regions.

With respect to the variable region of the beta chain, referred to as a V$\beta$, the nomenclature used herein to identify specific V$\beta$s follows that of Kimura et al., *Eur. J. Immuno.* 17:375–383 (1987).

During lymphocyte maturation, single V, (D) and J gene segments are rearranged to form a functional gene that determines the amino acid sequence of the TCR expressed by that cell. Since the pool of V, (D) and J genes which may be rearranged is multi-membered and since individual members of these pools may be rearranged in virtually any combination, the complete TCR repertoire is highly diverse and capable of specifically recognizing and binding the vast array of binding partners to which an organism may be exposed. However, a particular T cell will have only one TCR molecule and that TCR molecule, to a large degree if not singly, determines the specificity of that T cell for its binding partner.

Animal models have contributed significantly to the understanding of the immunological mechanisms of autoimmune disease. One such animal model, experimental allergic encephalomyelitis (EAE), is an autoimmune disease of the central nervous system that can be induced in mice and rats by immunization with myelin basic protein (MBP). The disease is characterized clinically by paralysis and mild wasting and histologically by a perivascular mononuclear cell infiltration of the central nervous system parenchyma. The disease pathogenesis is mediated by T cells having specificity for MBP. Multiple clones of MBP-specific T cells have been isolated from animals suffering from EAE and have been propagated in continuous culture. After in vitro stimulation with MBP, these T cell clones rapidly induce EAE when adoptively transferred to healthy hosts. Importantly, these EAE-inducing T cells are specific not only for the same antigen (MBP), but usually also for a single epitope on that antigen. These observations indicate that discrete populations of autoaggressive T cells are responsible for the pathogenesis of EAE.

Analysis of the TCRs of EAE-inducing T cells has revealed restricted heterogeneity in the structure of these disease-associated receptors. In one analysis of 33 MBP-reactive T cells, only two alpha chain V region gene segments and a single alpha chain J region gene segment were found. Similar restriction of beta chain TCR gene usage was also observed in this T cell population. Only two beta chain V region segments and two J region gene segments were found. More importantly, approximately eighty percent of the T cell clones had identical amino acid sequences across the region of beta chain V-D-J joining. These findings confirm the notion of common TCR structure among T cells with similar antigen specificities and indicate that the TCR is an effective target for immunotherapeutic strategies aimed at eliminating the pathogenesis of EAE.

An alternative mechanism for T cell activation has been suggested in which endogenous and exogenous superantigens have been shown to mediate T-cell stimulation as described, for example, in White et al., *Cell* 56:27–35 (1989) and Janeway, *Cell* 63:659–661 (1990).

The present invention provides an effective method of immunotherapy for diabetes which avoids many of the problems associated with current methods of treatment. By administering the TCRs or fragments thereof of this invention the host's own immune system is mobilized to suppress the autoaggressive T cells. Thus, the suppression is persistent and may involve any or all immunological mechanisms in effecting that suppression. This multi-faceted response is more effective than the uni-dimensional suppression achieved by passive administration of monoclonal antibodies or ex vivo-derived regulatory T cell clones which requires a highly individualized therapeutic approach because of MHC non-identity among humans in order to avoid graft versus host reactions. The methods of the present invention are also more effective than vaccination with attenuated disease-inducing T cells that lack specificity for the protective antigen on the surface of a particular T cell as well as the variable induction of immunity to that antigen. In addition, vaccination with attenuated T cells is plagued by the same labor intensiveness and need for individualized therapies as noted above for ex vivo derived regulatory T cell clones.

As they relate to diabetes, the compositions of the present invention comprise TCRs and fragments thereof corresponding to specific T cells that mediate diabetes. The peptides can be whole TCRs substantially purified from T cell clones, individual T cell receptor chains (for example, alpha, beta, etc.) or portions of such chains, either alone or in combination. The compositions can be homogenous, for example, a single TCR or fragment, or can be composed of more than one type of peptide, each of which corresponds to a different portion of the TCR. Further, these peptides can vary in amino acid sequences or length from TCRs that contribute to diabetes so long as they can elicit or affect a regulatory response. Such peptides can be between about 5 and 125 amino acids in length.

In a further specific embodiment, T cell receptors, whole T cells or fragments of TCRs that contain Vβ6 or Vβ14 can be administered to an individual having diabetes. The effect on the immune system generated in the individual can neutralize or kill T cells having Vβ6 or Vβ14 and, thus, prevent or treat the deleterious effects of such VB-bearing T cells.

As used herein, "Vβ36.1" refers to a specific human β-chain variable region. Vβ6.1 has the amino acid sequence shown in FIG. 1. The CDR2 sequence of Vβ6.1 is LIY-FQGTGAADDSGL. Kimura, N. et al., *Eur. J. Immunol.* 17:375–383 (1987).

As used herein, "Vβ6.6/6.7" refers to two separate human variable gene regions encoding identical amino acid sequences of specific human β-chain variable regions. Vβ6.6/6.7 has the following amino acid sequence: IYFQGNSAPDKSGL. Kimura, N. et al., *Eur. J. Immunol.* 17:375–383 (1987).

As used herein, "Vβ14" refers to a specific human β-chain variable region. Vβ14 has the following amino acid sequence: YYSMNVEVTDKGDV. Li, Y. et al., *J. Exp. Medicine,* 174:1537–1547 (1991).

Figure 1:
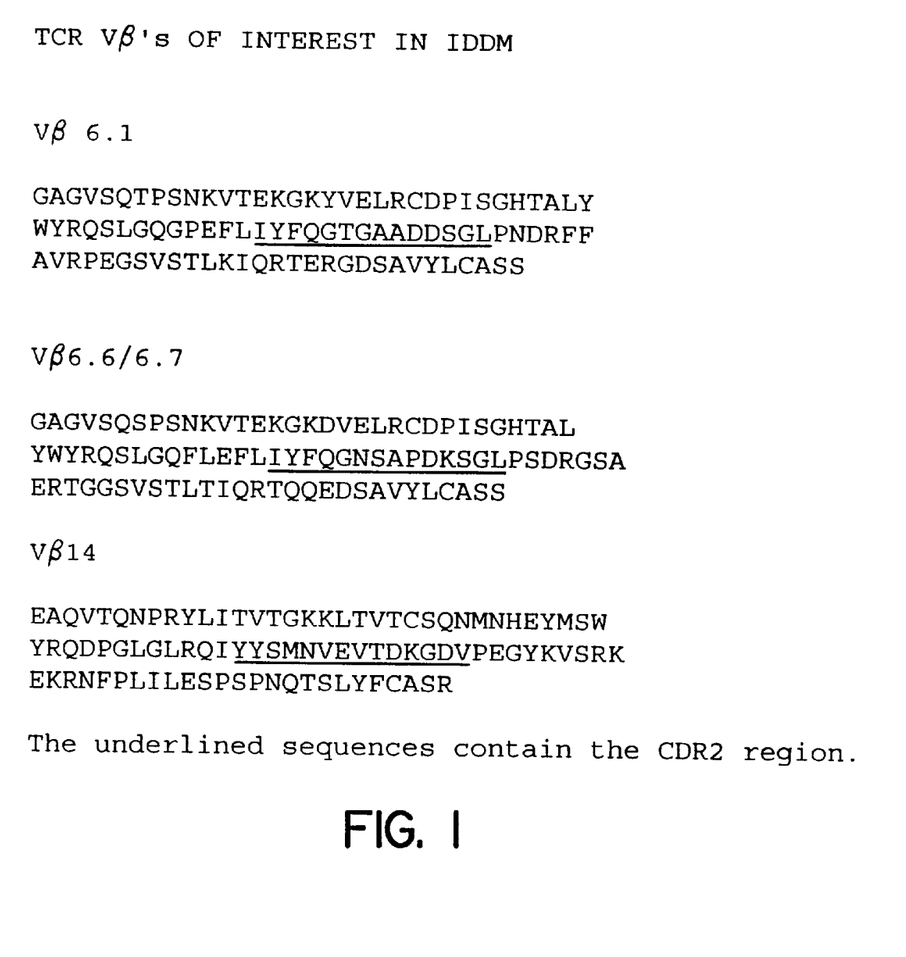
FIG. 1 provides the amino acid sequence of the variable regions of the Vβ6.1, Vβ6.6/6.7 and Vβ14 chains. The underlined portion are the CDR3 regions.

The hypervariable or junctional regions are useful for the compositions of the present invention. Hypervariable regions useful in the present invention include CDR1, CDR2, CDR3 and CDR4. The amino acid sequences of the CDR1, CDR2 and CDR4 hypervariable regions for Vβ6 or Vβ14 are shown in FIG. 1.

The CDR3, also known as the V(D)J region, is useful as a composition of the present invention since T cell immunity elicited by peptides corresponding to this region is expected to be highly specific for a particular antigen. Due to the recombination of the V, D and J region genes prior to maturation, the amino acid sequence across these regions is virtually unique to each T cell and its clones.

However, as a germ-line element, the CDR2 region is also useful in diabetes. In diabetes studies, the results indicate a limited number of Vβs among the activated T cells. Thus, peptides corresponding to the CDR2 region are viable alternatives for use as compositions of the present invention. For example, the CDR2 region of Vβ6.1: IYFQGT-GAADDSGL G, of Vβ6.6/6.7: IYFQGNSAPDKSGL G, or of Vβ14: YYSMNVEVTDKGDV G, can be used.

Modifications in these sequences that do not affect the ability of the receptor or a fragment thereof to act as an immunogen to stimulate the desired effect on the immune system are contemplated and are included in the definition of TCR fragment. The variable region can be joined with any D and J segment of the TCR. Further, representative fragments of Vβ6.1, Vβ6.6/6.7 and Vβ14 are also included in the definition of "Vβ6.1, Vβ6.6/6.7 and Vβ14," respectively.

In another embodiment, peptides can correspond to the Vβ regions that contain sequences of high homology which are conserved among pathogenic TCRs. These regions of conserved homology include the conventional CDRs, such as CDR1 and CDR2, which are common to T cells bearing the same Vβ, and also the superantigen binding site, which can be common to pathogenic TCRs bearing different Vβs. The superantigen binding site is also known to be in or around the CDR4 hypervariable region.

The compositions of the present invention comprise peptides of varying lengths corresponding to the TCR or fragments thereof capable of causing an effect on the immune system. The peptides can correspond to regions of the TCR which distinguish that TCR from other nonpathogenic TCRs. Such specific regions can, for example, be located within the various region(s) of the respective TCR polypeptide chains, for example, a short sequence spanning the V(D)J junction, thus restricting the effect on the immune system solely to those T cells bearing this single determinant.

The compositions are administered to an individual exhibiting or at risk of exhibiting diabetes. Definite clinical diagnosis of diabetes warrants the administration of the relevant disease-specific TCR compositions. Prophylactic applications are warranted in diseases where the autoimmune mechanisms precede the onset of overt clinical disease. Thus, individuals with familial history of disease and predicted to be at risk by reliable prognostic indicators could be treated prophylactically to interdict autoimmune mechanisms prior to their onset.

TCR peptides can be administered in many possible formulations, including pharmaceutically acceptable media. In the case of a short peptide, the peptide can be conjugated to a carrier, such as KLH, in order to increase its ability to cause an effect on the immune system. The composition can include or be administered in conjunction with an adjuvant, of which several are known to those skilled in the art. After initial immunization with the vaccine, further boosters can be provided. The compositions are administered by conventional methods, in dosages which are sufficient to cause an effect on the immune system. Such dosages can be easily determined by those skilled in the art.

Appropriate peptides to be used for administration can be determined as follows. Disease-inducing T cell clones reactive with the target antigens are isolated from affected individuals. Such T cells are obtained preferably from the site of active autoaggressive activity such as a psoriatic lesion. Alternatively, such T cells can be obtained from blood of affected individuals. The TCR genes from these autoaggressive T cells are then sequenced. Polypeptides corresponding to TCRs or portions thereof that are selectively represented among disease inducing T cells (relative to non-pathogenic T cells) can then be selected as vaccines and made and used as described above. An alternative method for isolating pathogenic T cells is provided by Albertini in PCT Publication No. WO88/10314, published on Dec. 29, 1988.

Alternatively, the compositions can comprise anti-idiotypic antibodies which are internal images of the peptides described above. Methods of making, selecting and administering such anti-idiotype vaccines are well known in the art. See, for example, Eichmann, et al., *CRC Critical Reviews in Immunology* 7:193–227 (1987), which is incorporated herein by reference.

In a further aspect of the present invention, methods of preventing the proliferation of T cells associated with diabetes are also contemplated. Such methods include determining a T cell receptor binding partner according to the above methods and administering an effective amount of such binding partner in an appropriate form to prevent the proliferation of the T cells. The methods can be used, for example, to build a tolerance to self antigens as in the case of an autoimmune disease.

The present invention also relates to methods of preventing or reducing the severity of diabetes by inhibiting the binding of a T cell receptor to its TCR binding partner in order to prevent the proliferation of T cells associated with diabetes. Ligands that are reactive with the T cell receptor or its binding partner at binding sites that inhibit the T cell receptor attachment to the binding partner can be used. Such ligands can be, for example, antibodies having specificity for the T cell receptor or its binding partner.

The invention also provides a method of preventing or reducing the severity of diabetes in an individual comprising cytotoxically or cytostatically treating Vβ-containing T-cells, particularly Vβ6.1, Vβ6.6/6.7 or Vβ14, in the individual. The Vβ-containing T cells are treated with a cytotoxic or cytostatic agent that selectively binds to the Vβ region of a T cell receptor that mediates diabetes. The agent can be an antibody attached to a radioactive or chemotherapeutic moiety. Such attachment and effective agents are well known in the art. See, for example, Harlow, E. and Lane, Antibodies, A Laboratory Manual, Cold Spring Harbor Laboratory (1988), which is incorporated herein by reference.

As noted, the invention provides the discovery that specific variable regions of the β-chains of three TCRs, designated Vβ6.1, Vβ6.6/6.7 or Vβ14, are closely associated with diabetes in human subjects. This discovery allows for the detection, prevention and treatment of diabetes using the methodology set out in this invention.

Specifically, the invention provides a method of diagnosing or predicting susceptibility to diabetes in an individual comprising detecting T cells having the β-chain variable region from Vβ6 or Vβ14 in a sample from the individual, the presence of abnormal levels of such Vβ-containing T cells indicating the pathology or susceptibility to the pathology. The Vβ-containing T cells can be qualitatively or quantitatively compared to that of normal individuals. Such diagnosis can be performed, for example, by detecting a portion of the Vβs that does not occur on non-diabetes associated β-chain variable region T-cell receptors. The Vβs of the present invention can be detected, for example, by contacting the Vβs with a detectable ligand capable of specifically binding to the individual Vβs. Many such detectable ligands are known in the art, e.g. an enzyme linked antibody. Alternatively, nucleotide probes, complementary to the individual Vβ of interest, encoding nucleic acid sequences can be utilized to detect such Vβ-containing T cells.

The invention also provides a method of preventing or reducing the severity of diabetes comprising preventing the attachment of a Vβ6 or Vβ14-containing T-cell receptor to its binding partner. In one embodiment, attachment is prevented by binding a ligand to Vβ6.1, Vβ6.6/6.7, or Vβ14. In an alternative embodiment, attachment is prevented by binding a ligand to the Vβ6 or Vβ14 binding partner. Attachment can be prevented by known methods, e.g. binding an antibody to the individual Vβs or to its binding partner in order to physically block attachment.

The present invention further relates to a method of preventing or reducing the severity of diabetes by gene therapy. This method involves the use of vectors having an expression control sequence operatively linked to a nucleic acid molecule encoding a polypeptide. The nucleic acid molecule can be DNA or RNA. The polypeptide can be a TCR or a fragment thereof capable of causing an effect on the immune system, or an anti-idiotype antibody that can be used as a composition in the present invention. Such DNA or RNA can be isolated by standard methods known in the art. The isolated nucleic acid can then be inserted into a suitable vector by known methods. An expression control sequence is operatively linked to a nucleic acid molecule when it directs the transcription and translation of that molecule in an appropriate host cell. This includes provision of appropriate start and stop codons. Expression vectors and their use are well known to the art. Such methods are described, for example, in Sambrook et al., *Molecular Cloning—A Laboratory Manual,* Cold Spring Harbor Laboratory, Cold Spring Harbor, N.Y., (1989) which is incorporated herein by reference.

The vector is subsequently administered directly into a tissue of an individual. Preferably, the DNA or RNA-containing vector is injected into the skeletal muscle of the individual. For example, a 1.5 cm incision can be made to expose the quadricep muscles of the subject. A 0.1 ml solution containing from 10–100 μg of a DNA or RNA plasmid and 5–20% sucrose is injected over 1 minute into the exposed quadricep muscles about 0.2 cm deep. The skin is thereafter closed. The amount of DNA or RNA vector can range from 10 to 100 μl of hypotonic, isotonic or hypertonic sucrose solutions or sucrose solutions containing 2 mM CaCl$_3$. The plasmid containing solutions can also be administered over a longer period of time, for example, 20 minutes, by infusion. The in vivo expression of the desired gene can be tested by determining an increased production of the encoded polypeptide by the subject according to methods known in the art or as described, for example, in Wolff et al., Science 247:1465–1468 (1990).

It is believed that the treated cells will respond to the direct injection of DNA or RNA by expressing the encoded polypeptide for at least about 60 days. Thus, the desired TCR, fragment capable of causing an effect on the immune system or anti-idiotype antibody can be effectively expressed by the cells of the individual as an alternative to vaccinating with such polypeptides.

The present invention also relates to vectors useful in the gene therapy methods and can be prepared by methods known in the art. Compositions containing such vectors and a pharmaceutically acceptable medium are also provided. The pharmaceutically acceptable medium should not contain elements that would degrade the desired nucleic acids.

The following example is intended to illustrate but not limit the invention.

EXAMPLE

PREFERENTIAL USAGE OF Vβ6 or Vβ14 IN DIABETES

The T-cell receptor β (TCR-β) gene of wildtype and hprt mutant T-cell isolates from diabetic and normal individuals have been sequenced. The hprt mutants from diabetics will have a different TCR-β repertoire in terms of both Vβ usage and extent of clonality than mutants from normals or wildtype from both groups. All wildtype isolates from normals and diabetes patients have a similar TCR-β distribution because they are being drawn from the same in vivo T-cell population, i.e., the non-dividing G$_0$ subset of T-cells that make up the majority. Finally, mutant isolates from normal individuals are also generated because of in vivo cell division. However, the distribution of TCR's in this set does not resemble that seen in diabetes because they did not arise in the context of this immunologically mediated disease. They should more closely resemble wildtype populations.

The hprt cloning assay was utilized to isolate wildtype and 6-thioguanine resistant T-cell isolates from normal and diabetic individuals. These isolates were expanded clonally in vitro and 1–5×10$^6$ cells harvested for RNA extraction. The cells are centrifuged and resuspended in 400 μl of cell lysis solution (Bio 101) and total RNA extracted by using the RNaid Plus kit (Bio 101) according to the manufacture's (San Diego, Calif.) directions. The RNA was eluted from the RNAMATRIX in 25 μl of DEPC-treated water and stored at –70° C. A 2 μl aliquot of RNA is used to make cDNA. The cDNA reaction was performed in a 12 μl volume consisting of 4.66 μl DEPC water, 1.2 μl AU$^{+Mg}$ buffer (500 mM Tris HCl pH=8.3, 400 nM KCl, 60 mM MgCl$_2$, 10 mM DTT), 3.6 μl of 2.5 mM dNTP's, 0.24 μl human Cβ-external primer (24 pmoles/reaction) (sequence= CCAGAAGGTGGCCGAGAC) and 0.3 μl AMV reverse transcriptase enzyme (8 U/μl, Promega). Multiple samples were usually processed and cocktails of reagents made in reactions. The reaction was incubated for one hour at 42° C. followed by a 15 minute incubation at 94° C. to denature the enzyme. The samples were then placed on ice.

The following primers were used for two rounds of PCR: Vβ consensus primer T(G/T)T(A/C/T)(C/T)TGGTA(C/T)(A/C)(A/G)(A/T)CA (both rounds), Cβ-external (first round), Cβββ-internal GCGGCTGCTCAGGCACTA (second round). For the first round, 0.8 μl Au$^{Mg}$ buffer (500 mM Tris HCl pH=8.3, 400 mM KCl, 10 mMDTT), 0.16 μl Cβ-external primer (16pmoles/reaction), 0.4 μl Vβ-consensus primer (40 pmoles/reaction), 2,4 μl dNTP's (2.5 mM), 4.24 μl HPLC H$_2$O, and 1 unit of taq polymerase (0.2 μl) were added to each sample. The PCR profile used is cycle 1:94° C. 3min, 37° C. 2 min, 72° C. 2 min followed by a 10 minute extension at 72° C. The second round of PCR was a 75 μl Cetus buffer, 0.75 μl Cβ-internal primer (75 pmoles/reaction), 5.25 μl Vβ-consensus primer (525 pmoles/ reaction), 16 μl dNTP's (1.25 mM), 48.75 μl HPLC H$_2$O and 5 units of taq enzyme (1 μl). The PCR was done in a PE 9600 under the same profile as above with the exception that a total of 37 cycles are completed.

Upon completion of the PCR, the entire volume of the reaction was run on a 1.5% agarose gel and the product visualized by ethidium bromide staining. A gel slice containing the product of interest (~500 bp) was cut out ot the gel and Gene Cleaned (Bio 101). The DNA was eluted in 10–30 μl of HPLC H$_2$O, the volume depending on the intensity of the band cut out.

The purified product was sequenced using the Taq DyeDeoxy Terminator Cycle Sequencing kit (Applied Biosystems, Foster City, Calif.) according to the manufacturers protocol. 7.3 μl of the purified product (approximately 100 ng) is added to 9.5 μl of reaction pre-mix and 3.2 μl of Cβ-seq (3.2 pmoles/reaction)(sequence= CGACCTCGGGTGGGAACA). The sequencing products were purified through G-50 sephadex columns and run on an ABI 373A (Applied Biosystems) automated sequencer. Vβ and Jβ gene segment usage was then established for each isolate and the VDJ junctional region sequence (CDR3) which defines the putative peptide binding site of the TCR.

A. Normal Individuals

Figure 2:
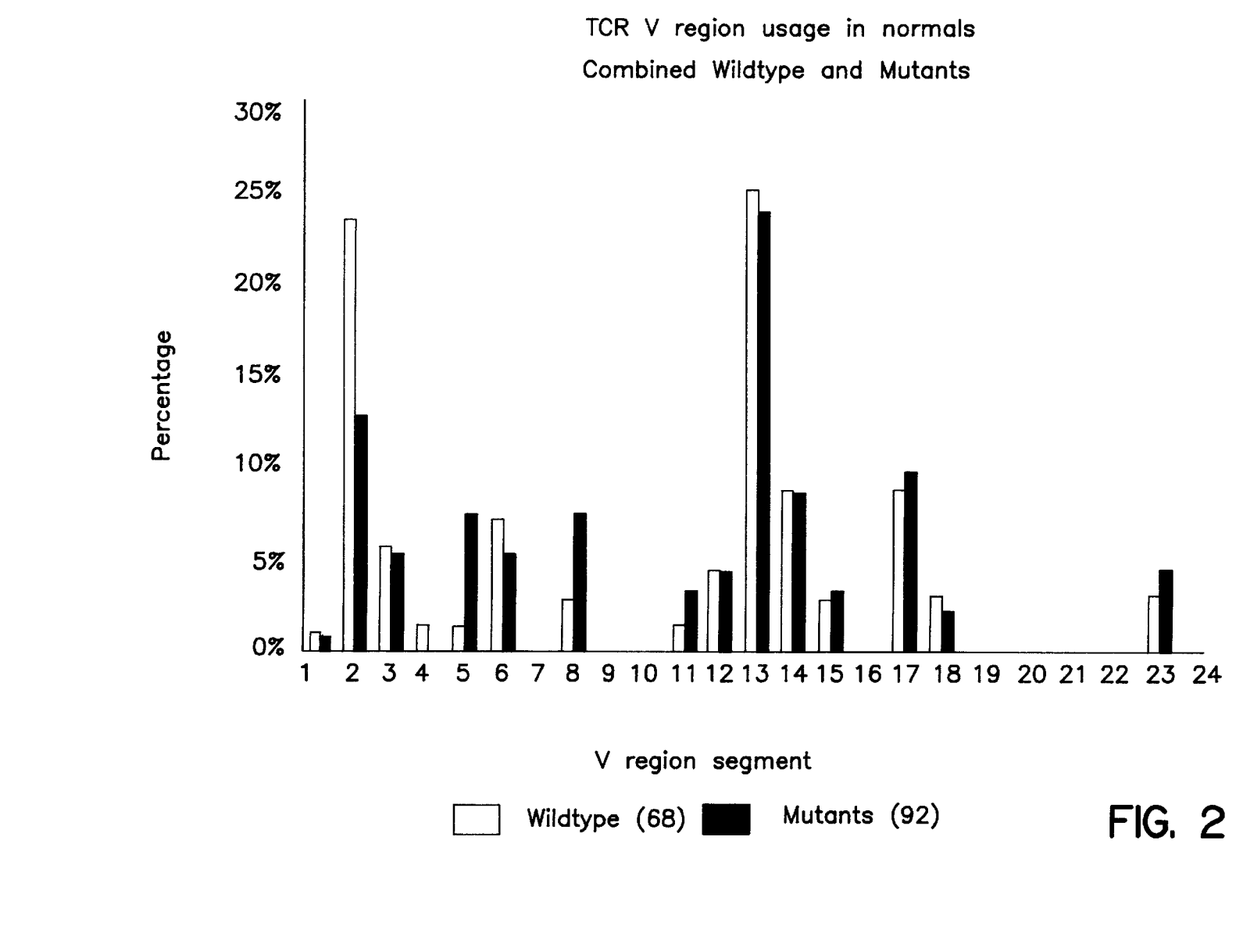
FIG. 2 provides the TCR V region usage in normals combined wildtype and mutants.

To determine the background TCR-β repertoire of the cloning system, PCR and sequencing analysis was completed on a total of 68 wildtype and 92 mutant isolates from three normal individuals. FIG. 2 displays the TCR VB distribution seen in these individuals. The results have been combined to give a general picture of Vβ usage in both the wildtype and mutant sets.

Actual variability seen between individuals was not extensive. The most frequent Vβ gene segment used was Vβ13. It was seen in approximately 25% of both the wildtype and mutant isolates analyzed. Vβ2 was also predominant; 24% of wildtype and 13% of all mutants used this Vβ. No other Vβ for either set of isolates was used at a percentage greater than 10%. The variability of Vβ usage observed between the wildtype and mutant sets from normal individuals does not appear, with the possible exception of Vβ2, to be significant. This result suggests that although the mutant set is probably derived from a population of recently dividing T-cells in vivo, there is no immunological activity that is broad enough to affect the Vβ distribution of the mutant set at this level of analysis.

The Vβ distribution observed in normals appears to differ from what has been described in the literature. Quantitative PCR has been used by others attempting to define the Vβ repertoire in normal humans. A comparison of the results to those seen by others show that some Vβ's are overrepresented in our sets (Vβ's 13, 2, 17, 14), while some are underrepresented (possible Vβ6, other Vβ's we have not recovered, including Vβ7). Each methodology has its limitation in its ability to define the true repertoire. This cloning and PCR approach can introduce a bias by providing to certain T-cells a growth advantage compared to other isolates. Furthermore, the clone by clone approach limits the total number of isolates that can be studied, making it difficult to look at large data sets. It is important to note, however, that the results in normals demonstrates that any possible bias in Vβ selection applies equally to both wildtype and mutant sets, thus allowing wildtype to serve as controls for mutants.

Analysis of the CDR3 region of each isolate at both the nucleotide and deduced amino acid level enables one to determine if there are clonal replicates in the data set for each individual. One wold not expect "clonal runs" in wildtype sets as one is drawing a limited number of isolates from an extremely large wildtype pool. Clonal runs in mutant sets is predicted under the rationale of surrogate selection, however, because if a proliferating clone mutates, it may continue to divide, thus making possible the recovery of siblings from a much smaller subset of T-cells in vivo. The extent of clonality observed should be partly dependent on the level of activation of the immune system. Normal individuals should have restricted clonality since commonly, any ongoing immune response will be limited in terms of extent and duration. Our results in normals fit the expected results. There was no clonality observed in the wildtype sets of the three individuals and the clonality levels of the mutants are consistent with what has been seen historically in normals using Southern blot analysis to determine clonality.

B. Diabetics

Figure 3:
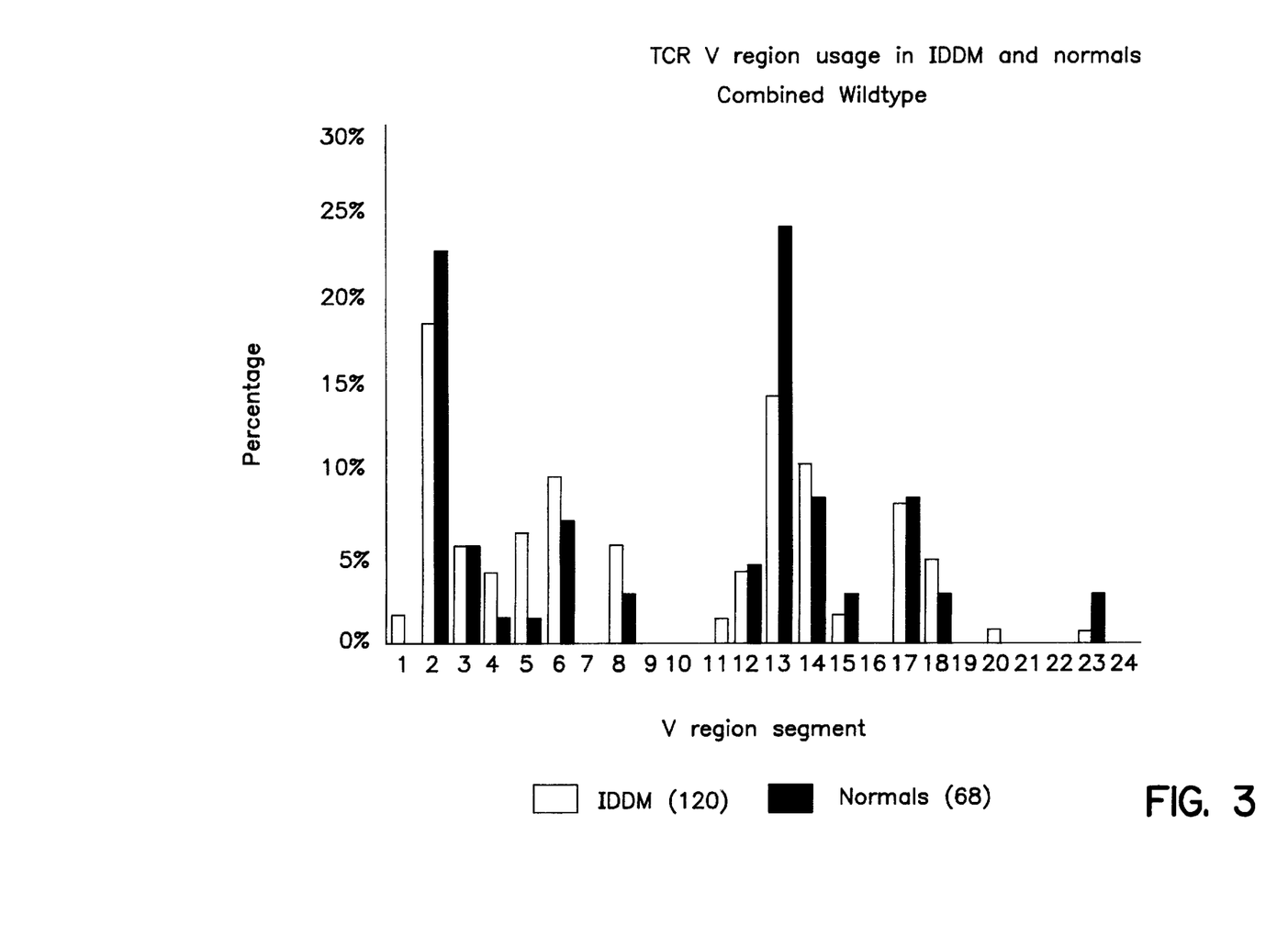
FIG. 3 provides the TCR V region usage in IDDM and normals combined wildtype.

Having assessed the TCR Vβ repertoire in normal individuals, PCR and sequencing analysis was completed on a total of 120 wildtype and 199 mutant isolates from eight patients with IDDM (10 blood samples). FIG. 3 displays the combined TCR Vβ distribution of wildtype from the diabetics and compares it to the distribution seen in normal wildtype. Again, a similar pattern of VB usage emerges. Predominating Vβ's seen in this wildtype set includes Vβ13 (15%) and Vβ2 (19%). Both Vβ6 or Vβ14 are used around 10% of the time and Vβ17 approaches that figure. Absent Vβ's include Vβ7, 9, 10, 11, 16, 19, 21, 22, 24. CDR3 analysis reveals that all isolates were independently derived, i.e., there was no clonality evident.

Figure 4:
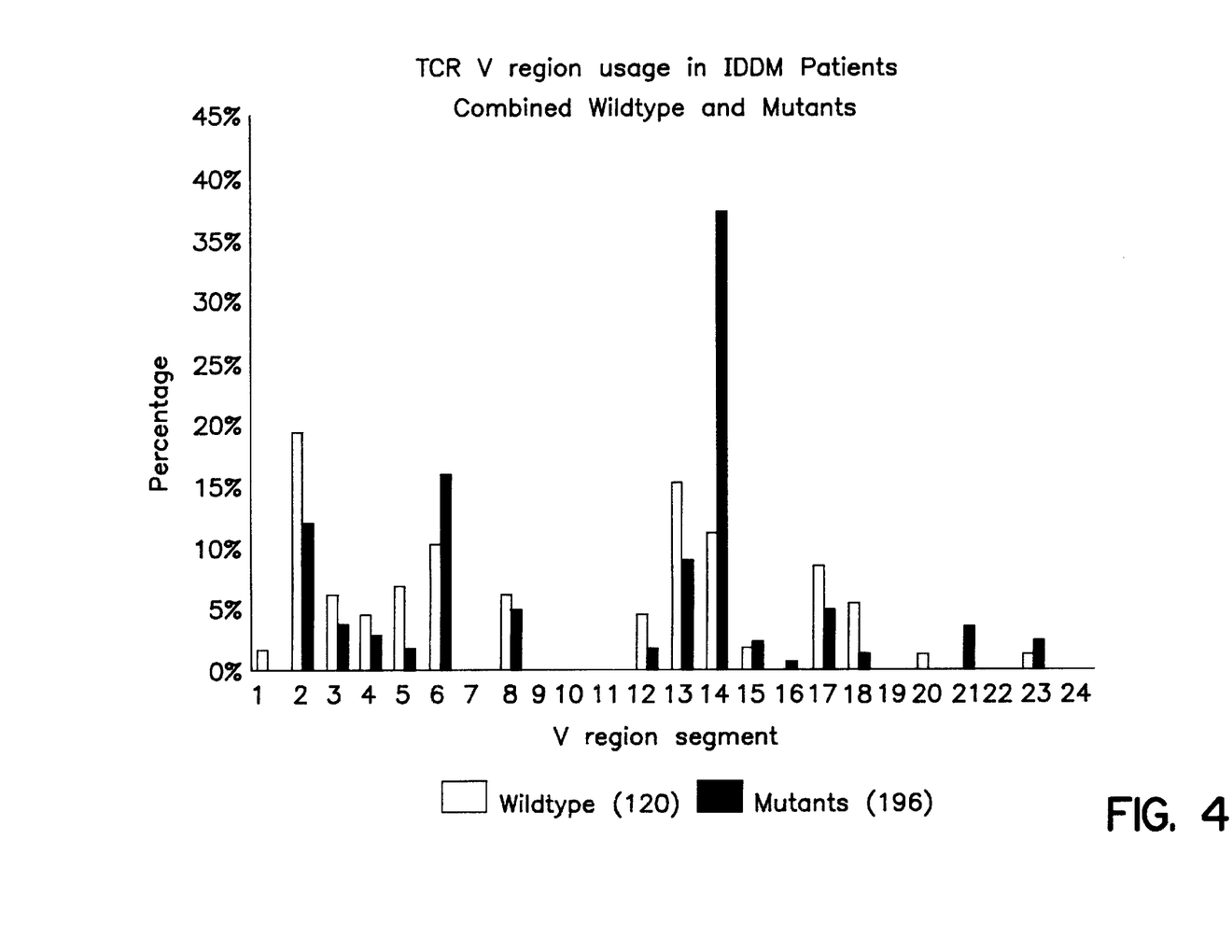
FIG. 4 provides the TCR V region usage in IDDM patients combined wildtype and mutants.

In comparing the combined mutants from diabetes to their wildtype, interesting differences in the Vβ distribution were revealed (FIG. 4). Greater than one of three mutants analyzed used the Vβ14 gene segment. Vβ6 appears to also be slightly elevated whereas the majority of other Vβs such as Vβ2 and Vβ13 are utilized to a lesser extent. Looked at individually, however, the diabetic patients individually, however, they do not show a similar distribution of Vβ usage. Three patients (FIG. 5) have the vast majority of mutants analyzed expressing Vβ14. In one patent,(MF605 Table I) 17 of 21 were identical. Therefore, over 80% of all mutants analyzed in this experiment were derived from the same in vivo dividing clone. Furthermore, 23 of 29 mutants sequenced from a subsequent blood sample taken ten months later were part of this clone. None of a total of 22 wildtype (MF669, Table I) from both experiments combined revealed this sequence. These results clearly demonstrate that surrogate selection has "captured" an in vivo activated T-cell clone that may be important in the pathogenesis of autoimmune diabetes.

Figure 5:
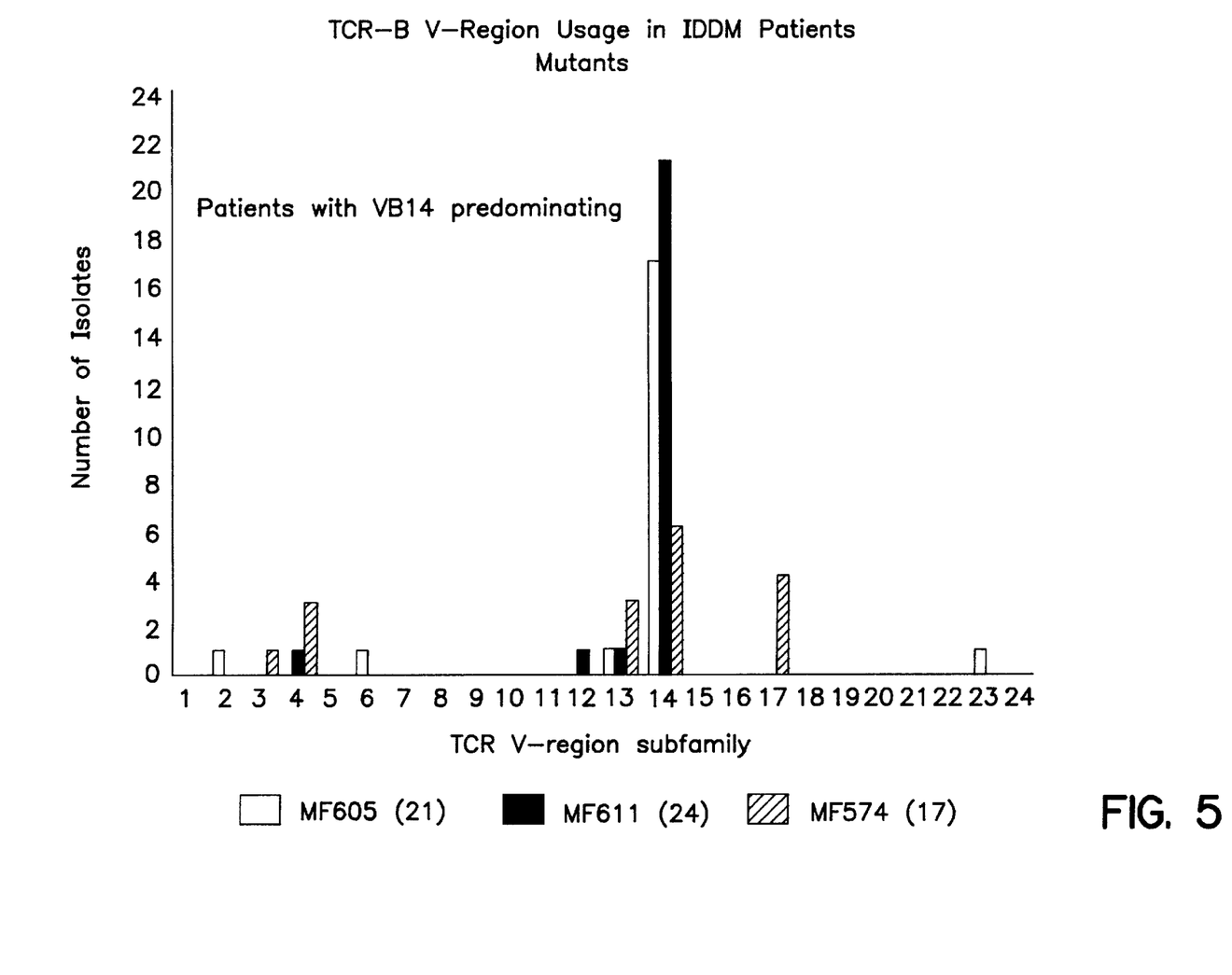
FIG. 5 provides the TCR-β V-region usage in IDDM patients mutants.

As shown in FIG. 5, an additional two patients also showed Vβ14 predominance, further implicating this Vβ as being important in diabetes. Of 24 mutants studied in MF611, 21 exhibited Vβ14, See Table I. Sequencing of the CDR3 region broke down these isolates into one large clonal run (16-mer), a triplet, and two independent isolates. MF574 (Table I)displayed a 6-mer that uses Vβ14 and also additional clonal runs that utilized Vβ17 (4-mer) and Vβ4 (triplet).

TABLE I

IDDM Patients with Vβ 14.1 Predominance

| Patient | # Mutants Sequenced | # Mutants Vβ 14 pos. | Clonality |
|---|---|---|---|
| MF605[1] | 21 | 17 | 17-mer |
| MF669[1] | 29 | 23 | 23-mer[2] |
| MF611 | 24 | 21 | 16-mer |
|  |  |  | 3-mer |
| MF574 | 17 | 6 | 6-mer |

[1]same patient with blood samples taken 10 months apart.
[2]these isolates have the exact sequence as the 17-mer in MF605.

It is important to note that the treatment these patients are receiving cannot be solely responsible for the results described. All diabetes patients chosen for our study were part of an immuran program being conducted at the University of Florida in Gainseville. Two of three patients entered into the program received the immunosuppressive drug azathioprine (immuran) while the remainder received a placebo. This drug provides an in vivo selection for T-cell hprt mutants and thus, serves to amplify the mutant frequency values we obtain when using our cloning assay in these patients. MF611 and MF574 were both on azathioprine at the time the blood sample was drawn. However, MF605 (MF669) was not receiving the drug.

Figure 6:
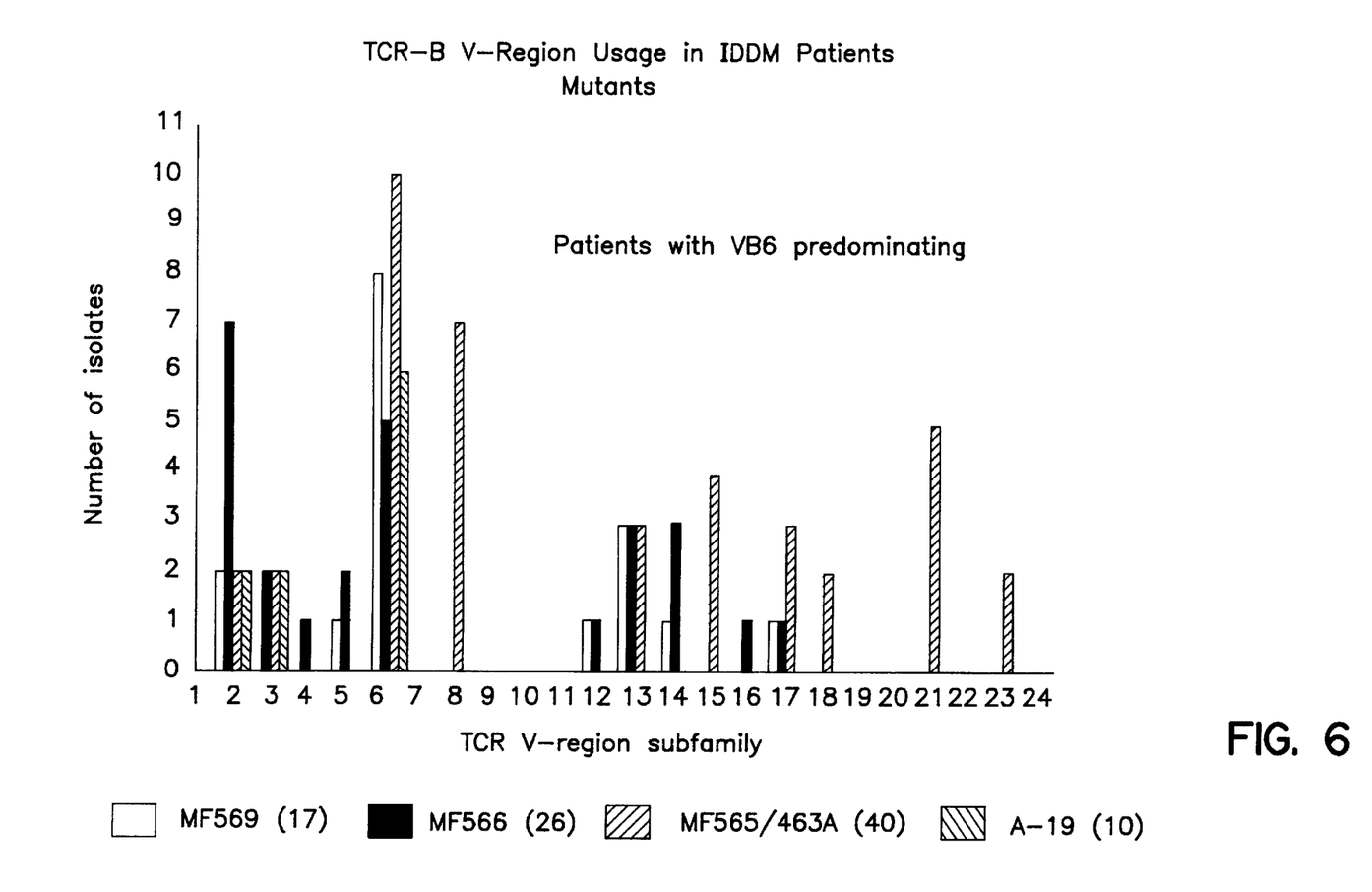
FIG. 6 provides the TCR-β V-region usage in IDDM patients mutants.
Figure 7:
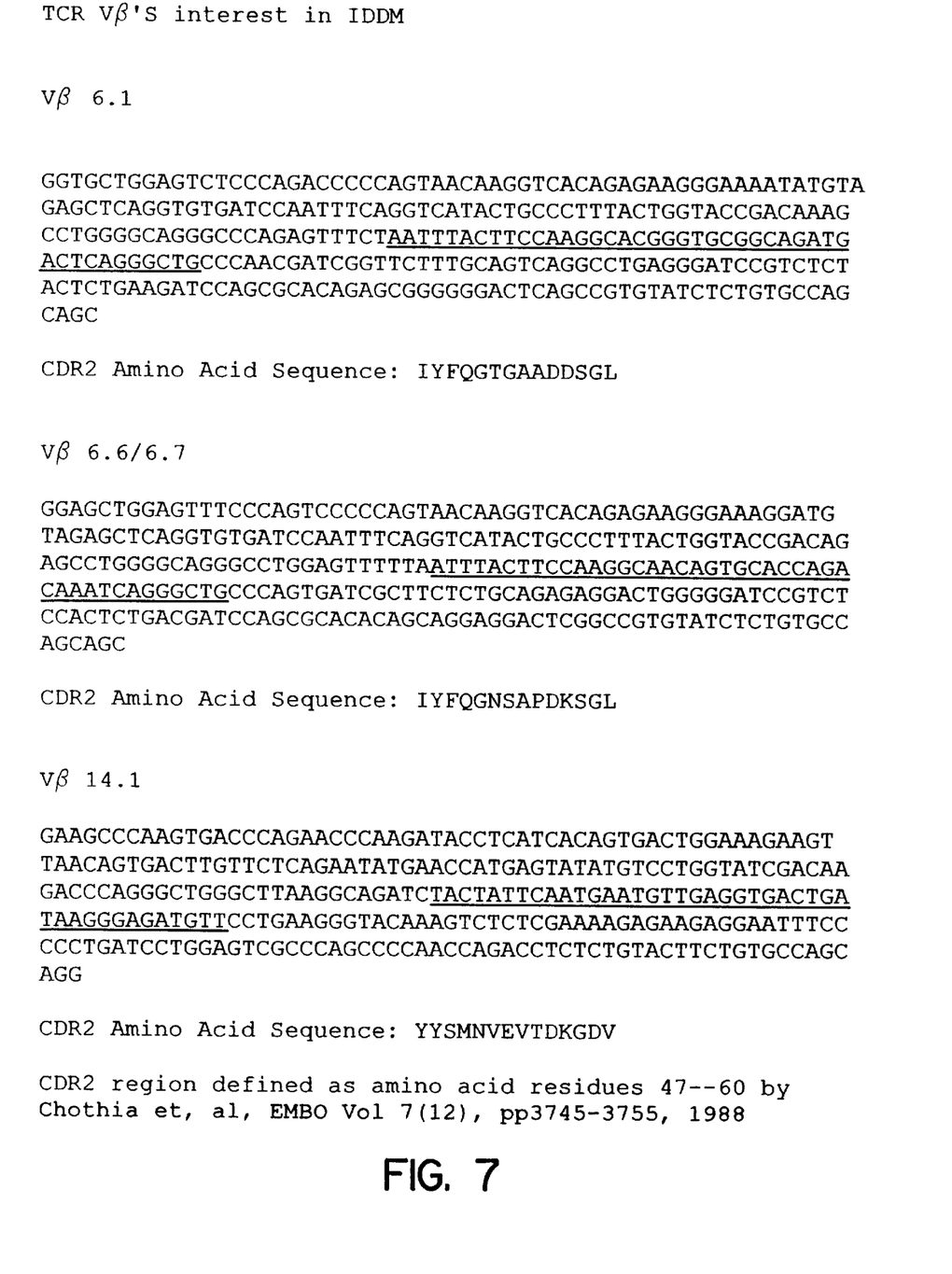
FIG. 7 provides the nucleic acid sequences for Vβ6.1, Vβ6.6/6.7 and Vβ 14.

Other patients appeared to have Vβ6 predominance within their mutant sets although the results are not quite as dramatic as seen in the previously described patients. FIG.

6 described the Vβ distribution of four patients (five samples). Of 17 mutants studied from MF569 (Table II), eight used Vβ6 (47%; a 5-mer and three independent isolates by CDR3 analysis). In the wildtype set of this patient, only four of 32 isolates used Vβ6 (12.5%). In the other three patients, (Table II) Vβ6 was used twice as frequently in the combined mutant set as compared to the combined wildtype set (mutants: 21/76, 27.6%; wildtype: 6/48, 12.5%).

TABLE II

IDDM Patients with Vβ 6 Predominance

| Patient | # Mutants Sequenced | # Mutants Vβ 6 pos. | Clonality |
|---------|---------------------|---------------------|-----------|
| A-19    | 10                  | 5 (Vβ 6.6/7)        | —         |
|         |                     | 1 (Vβ 6.9)          |           |
| MF463A  | 20                  | 6 (Vβ 6.6/7)        | 6-mer     |
|         |                     | 1 (Vβ 6.1)          |           |
|         |                     | 1 (Vβ 6.3)          |           |
|         |                     | 1 (Vβ 6.9)          |           |
| MF566   | 26                  | 3 (Vβ 6.9)          | 3-mer     |
|         |                     | 2 (Vβ 6.6/7)        |           |
| MF569   | 17                  | 6 (Vβ 6.1)          | 5-mer     |
|         |                     | 2 (Vβ 6.6/7)        |           |

Although the invention has been described with reference to the presently-preferred embodiments, it should be understood that various modifications can be made without departing from the spirit of the invention. Accordingly, the invention is limited only by the claims that follow.

We claim:

1. A method of reducing the severity of diabetes in an individual comprising administering a single chain peptide having an amino acid sequence of a non-constant region of a human β-chain of a Vβ6.1, Vβ6.6/6.7 or Vβ14-containing T cell receptor present on the surface of T cells mediating diabetes that reduces the severity of diabetes, or a modified peptide having substantially the same amino acid sequence as said single chain peptide, wherein said modified peptide induces substantially the same immune response as said single chain peptide and reduces the severity of diabetes.

2. The method of claim 1, wherein said non-constant region is the CDR1, CDR2 or CDR4 region of said β-chain.

3. The method of claim 2, wherein said CDR2 region has the Vβ6.1 sequence IYFQGTGAADDSGL.

4. The method of claim 2, wherein said CDR2 region has the Vβ6.6/6.7 sequence IYFQGNSAPDKSGL.

5. The method of claim 2, wherein said CDR2 region has the Vβ4 sequence YYSMNVEVTDKGDV.

6. The method of claim 1, further comprising administering two or more single chain peptides each having an amino acid sequence of a non-constant region of a T cell receptor present on the surface of T cells mediating diabetes that reduces the severity of diabetes, wherein at least one of said peptides has an amino acid sequence of a non-constant region of a β-chain of a Vβ6.1, Vβ6.6/6.7 or Vβ14-containing T cell receptor or a modified peptide having substantially the same amino acid sequence as said single chain peptide, wherein said modified peptide induces substantially the same immune response as said single chain peptide and reduces the severity of diabetes.

7. The method of claim 1, wherein the peptide is administered more than once.

8. The method of claim 1, wherein the peptide is administered in a formulation including an adjuvant.

9. A method of reducing the severity of diabetes in an individual comprising contacting Vβ6.1, Vβ6.6/6.7 or Vβ14-containing T cells specifically associated with diabetes with an effective amount of a cytotoxic or cytostatic agent specifically reactive with human Vβ6.1, Vβ6.6/6.7 or Vβ14 to inhibit the activity of said T cells.

10. The method of claim 9, wherein the agent is an antibody attached to a moiety selected from the group consisting of radioactive moieties, chemotherapeutic moieties and chemotoxic moieties.

11. A method of preventing or reducing the severity of diabetes in an individual comprising specifically inhibiting the attachment of a human Vβ6.1 Vβ6.6/6.7 or Vβ14-containing T cell receptor to its binding partner.

12. A method for diagnosing or predicting susceptibility to diabetes in an individual comprising contacting a sample isolated from the individual with a detectable ligand that specifically binds human Vβ6.1, Vβ6.6/6.7 or Vβ14 and determining the relative level of Vβ6.1, Vβ6.6/6.7 or Vβ14-containing T cells in said sample, wherein the presence of an abnormal level of Vβ6.1, Vβ6.6/6.7 or Vβ14 T cells is indicative of diabetes or susceptibility to diabetes.

13. A method of reducing the severity of diabetes in an individual, comprising administering to the individual a vector comprising an expression control sequence operatively linked to a nucleic acid encoding a single chain peptide having an amino acid sequence of a non-constant region of a human β-chain of a Vβ6.1, Vβ6.6/6.7 or Vβ14-containing T cell receptor present on the surface of T cells mediating diabetes, or a modified peptide having substantially the same amino acid sequence as said single chain peptide wherein said modified peptide induces substantially the same immune response as said single chain peptide and reduces the severity of diabetes.

14. The method of claim 13, wherein said non-constant region is the CDR1, CDR2 or CDR4 region of said β-chain.

15. The method of claim 14, wherein said CDR2 region has the Vβ6.1 sequence IYFQGTGAADDSGL.

16. The method of claim 14, wherein said CDR2 region has the Vβ6.6/6.7 sequence IYFQGNSAPDKSGL.

17. The method of claim 14, wherein said CDR2 region has the Vβ14 sequence YYSMNVEVTDKGDV.

18. A method of diagnosing or predicting susceptibility to diabetes in an individual comprising contacting a sample isolated from the individual with a nucleic acid probe that specifically binds a nucleic acid encoding human Vβ6.1, Vβ6.6/6.7 or Vβ14 and determining the relative level of human Vβ6.1, Vβ6.6/6.7 or Vβ14 T cells in said sample, wherein the presence of an abnormal level of Vβ6.1, Vβ6.6/6.7 or Vβ14 T cells is indicative of diabetes or susceptibility to diabetes.

* * * * *